United States Patent [19]

Stubbs et al.

[11] 4,017,541
[45] Apr. 12, 1977

[54] ORGANIC BUILDER

[75] Inventors: Christopher Edward Stubbs, Wirral, England; Jacobus Roelof Nooi, Vlaardingen; Hermanus Christoffel Kemper, Brielle, both of Netherlands

[73] Assignee: Lever Brothers Company, New York, N.Y.

[22] Filed: Sept. 15, 1975

[21] Appl. No.: 613,677

Related U.S. Application Data

[63] Continuation of Ser. No. 422,039, Dec. 5, 1973, abandoned.

[30] Foreign Application Priority Data

Dec. 7, 1972 United Kingdom ............ 56514/72

[52] U.S. Cl. ............................ 260/535 P; 252/132; 252/142; 252/156; 252/180; 252/546

[51] Int. Cl.$^2$ ......................................... C07C 59/14
[58] Field of Search ............................... 260/535 P

[56] References Cited

UNITED STATES PATENTS

| | | | |
|---|---|---|---|
| 3,293,176 | 12/1966 | White ............................. | 260/535 P |
| 3,725,260 | 4/1973 | Nelson et al. .................. | 260/535 P |

FOREIGN PATENTS OR APPLICATIONS

| | | | |
|---|---|---|---|
| 720,711 | 3/1973 | South Africa ................. | 260/535 P |

Primary Examiner—Paul J. Killos

[57] ABSTRACT

Particular, novel (dicarboxy)alkyl ethers are useful as builder ingredients in detergent compositions.

1 Claim, No Drawings

ORGANIC BUILDER

This is a continuation of application Ser. No. 422,039, filed Dec. 5, 1973, now abandoned.

The present invention relates to novel organic compounds, which are in particular useful as builders in detergent compositions.

Lately concern has been expressed about the possible attribution to the eutrophication of lake water by the commonly used tripolyphosphate builder salts in detergent compositions, and investigations have been made for replacements for such tripolyphosphate builder salts. Thus, for example, Dutch patent application No. 7,201,313 proposes particular polybasic ether carboxylic acids as builders for detergent compositions. Examples of such polybasic ether carboxylic acids are bis(O-carboxymethyl)ethylene glycol, tris(O-carboxymethyl)glycerol, O-carboxymethyltartronic acid, bis-(O-carboxymethyl) tartaric acid and the like. These compounds can be prepared, according to Dutch patent application No. 7,201,311, by reacting glycol, glycerol, esters of tartronic acid, and esters of tartaric acid with a diazoacetic ester in the presence of a Lewis acid and saponifying the resulting product.

It has now been found that particular novel (dicarboxy)alkyl ethers and salts thereof are useful builders, whose building capacity is comparable to that of a tripolyphosphate builder salt. The calcium-complexing ability of several of these (dicarboxy)alkyl ethers is better than that of several of the polybasic ether carboxylic acids according to the prior proposal.

The particular (dicarboxy)alkyl ethers of the invention are the di-O-malonyl derivatives of tartaric acid, propylene glycol and triethylene glycol, the mono-O-malonyl mono-O-acetyl derivative of ethylene glycol, and the mono- and di-O-succinyl derivatives of ethylene glycol, propylene glycol and diethylene glycol.

The (dicarboxy)alkyl ethers of the invention may be represented by the following general formula:

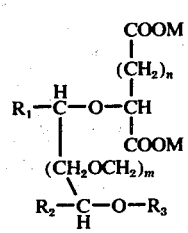

in which
$R_1 = H, -CH_3$ or $-COOM$
$R_2 = H$ or $-COOM$
$R_3 = H, -CH_2COOM$ or

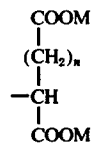

$n = 0$ or $1$
$m = 0, 1$ or $2$
$M = H, -CH_3, -C_2H_5$ or an alkalimetal
with the provisions that $R_2$ may only be $-COOM$ when $R_1 = -COOM$; furthermore, when $n = 0$, $R_3$ must be

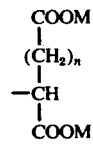

or $-CH_2COOM$, whereby $R_3$ may only be $-CH_2COOM$ when $R_1=R_2=H$ and $m = 0$ and the further provision that when $m = 1$, $n$ may only be 1.

The compounds of the invention may be prepared by reacting the relevant starting material with a diazomalonic ester or diazosuccinic ester in the presence of copper powder at a temperature of about 100° C in a manner known per se, followed by hydrolysis. Depending on the structure of the compound this hydrolysis is carried out in acid and/or in alkaline medium. These compounds can be used in the acid form, as well as in the form of suitable alkalimetal salts, such as sodium and potassium salts. The compounds with a pkCa of 4.8 and higher are preferred, in particular those with a pkCa of 6.1 and higher, such as TDM.

The following table represents the compounds of the invention, as well as their calcium complex constants.

| Compound | Code | $Pk_{Ca}$* | Starting material | Reagent |
| --- | --- | --- | --- | --- |
| Tartaric acid dimalonyl ether | TDM | 7.1 | dimethyl tartrate | dimethyl diazomalonate |
| Propylene glycol dimalonyl ether | PGDM | 6.1 | propylene glycol | dimethyl diazomalonate |
| Triethylene glycol dimalonyl ether | TEGDM | 4.8 | triethylene glycol | dimethyl diazomalonate |
| Ethylene glycol disuccinyl ether | HGDS | 4.9 | ethylene glycol | diethyl diazosuccinate |
| Propylene glycol disuccinyl ether | PGDS | 5.3 | propylene glycol | diethyl diazosuccinate |
| Propylene glycol monosuccinyl ether | PGMoS | 3.8 | propylene glycol | diethyl diazosuccinate |
| Diethylene glycol disuccinyl ether | DEGDS | 5.2 | diethylene glycol | diethyl diazosuccinate |
| Diethylene glycol monosuccinyl ether | DEGMoS | 3.8 | diethylene glycol | diethyl diazosuccinate |
| Ethylene glycol monosuccinyl ether | EGMoS | 5.0 | ethylene glycol | diethyl diazosuccinate |
| Ethylene glycol monoacetyl monomalonyl ether | EGAM | 4.8 | ethylene glycol | dimethyl diazomalonate/ diazoacetate |

*Determined according to: Schubert J. in "Methods of Biochemical Analysis", Vol. III. Ed. D. Glick, Interscience Publishers Inc., New York (1956).
conditions: pH = 10, temperature 25° C,/$\mu$ = 0.02

The novel compounds are useful builders for detergent compositions. They may be used in detergent compositions which contain an anionic, a nonionic, a cationic synthetic detergent or a soap or mixtures thereof, and which furthermore contain the normal detergent adjuvants.

The detergent compositions essentially include one or more anionic, nonionic, amphoteric or zwitterionic detergent active compounds, or mixtures thereof, in addition to the detergency builders.

The synthetic detergent active compounds which can be used in the compositions of the invention are preferably anionic detergent active compounds, which are readily available and relatively cheap, and mixtures thereof. These compounds are usually water-soluble alkali metal salts of organic sulphates and sulphonates having alkyl radicals containing from about 8 to about 22 carbon atoms. Examples of such synthetic anionic detergent active compounds are sodium and potassium alkyl sulphates, especially those obtained by sulphating the higher ($C_8$–$C_{18}$) alcohols produced by reducing the glycerides of tallow or coconut oil or synthetic alcohols derived from petroleum; sodium and potassium alkyl ($C_9$–$C_{20}$) benzene sulphonates, particularly sodium linear secondary alkyl ($C_{10}$–$C_{15}$) benzene sulphonates; sodium alkyl glyceryl ether sulphates, especially those ethers of the higher alcohols derived from tallow or coconut oil and synthetic alcohol derived from petroleum; sodium coconut oil fatty acid monoglyceride sulphates and sulphonates; sodium and potassium salts of sulphuric acid esters of higher ($C_9$–$C_{18}$) fatty alcohol-alkylene oxide, particularly ethylene oxide, reaction products, the reaction products of fatty acids such as coconut fatty acids esterified with isethionic acid and neutralised with sodium hydroxide; sodium and potassium salts of fatty acid amides of methyl taurine; alkane monosulphonates such as those derived by reacting alpha-olefins ($C_8$–$C_{20}$) with sodium bisulphite and those derived by reacting paraffins with $SO_2$ and $Cl_2$ or $O_2$, and then hydrolysing with a base to produce a random sulphonate; and olefin sulphonates, whch term is used to cover the material made by reacting olefins, particularly alpha-olefins, with $SO_3$ and then neutralising and hydrolysing the reaction product.

If desired, nonionic detergent active compounds may also be used. Examples include the reaction products of alkylene oxides, usually ethylene oxide, with alkyl ($C_6$–$C_{12}$) phenols, generally 5 to 25 EO; i.e. 5 to 25 units of ethylene oxide per molecule; the condensation products of aliphatic ($C_8$–$C_{18}$) alcohols with ethylene oxide, generally 6 to 30 EO, and products made by condensation of ethylene oxide with the reaction products of propylene oxide and ethylenediamine. Other so-called nonionic detergent active compounds include long chain tertiary amine oxides, long chain tertiary phosphine oxides and dialkyl sulphoxides.

Mixtures of detergent active compounds, for example mixed anionic or mixed anionic and nonionic compounds may be used in the detergent compositions, particularly to impart thereto controlled low sudsing properties. This is particularly beneficial for compositions intended for use in suds-intolerant automatic washing machines. Mixtures of amine oxides and ethoxylated nonionic compounds can also be beneficial.

Many suitable detergent active compounds are commercially available and are described in the literature, for example in "Surface Active Agents and Detergents" by Schwartz, Perry and Berch.

Amounts of amphoteric or zwitterionic detergent active compounds can also be used in the compositions of the invention but this is not normally desired due to their relatively high cost. If any amphoteric or zwitterionic detergent active compounds are used it is generally in small amounts in compositions based on the much more commonly used anionic or nonionic detergent active compounds.

The amount of the synthetic detergent active compound or compounds used is generally in the range of from about 10 to 50%, preferably about 15 to 30%, by weight of the compositions, depending on the desired properties. The ratio by weight of the detergency builder compounds of the present invention to the detergent active compounds, when used in laundering and hand dishwashing compositions, ranges generally from about 1:20 to about 20:1, preferably about 1:3 to 10:1, especially from about 1:1 to about 5:1. However, when the detergency builders are used in mechanical dishwashing compositions, the ratio of the detergency builder to detergent compound is generally from about 10:1 to about 50:1, as much smaller amounts of the detergent active compound are then usually employed.

The detergency builder compounds of the present invention can be used either as the sole detergency builders or where desired they can be used in conjunction with other detergency builders, examples of which include tetrasodium and tetrapotassium pyrophosphate, pentasodium and pentapotassium tripolyphosphate, trisodium and tripotassium nitrilotriacetate, ether polycarboxylates, citrates, oxidised starch and cellulose derivatives, especially those containing dicarboxyl units, sodium alkenyl ($C_{10}$–$C_{20}$) succinates, sodium sulpho-fatty acids, alkali metal carbonates and orthophosphates and polyelectrolyte builders such as sodium polyacrylate and sodium copolyethylene-maleate.

Other conventional materials may be present in the detergent compositions of the invention, for example soil-suspending agents, hydrotropes, corrosion inhibitors, dyes, perfumes, fillers, abrasives, optical brighteners, enzymes, suds boosters, suds depressants, germicides, anti-tarnishing agents, cationic detergents, fabric softening agents, chlorine-releasing agents, oxygen-liberating bleaches such as sodium perborate with or without peracid precursors, buffers and the like. The balance of the detergent compositions is water, for example in the range of from about 5 to 15% in the powdered detergent compositions.

The detergent compositions of the present invention may be in any of the usual physical forms for such compositions, such as powders, beads, flakes, bars, tablets, noodles, liquids, pastes, and the like. The detergent compositions are prepared and utilised in the conventional manner, for example in the case of powdered detergent compositions they may be made by spray-drying aqueous slurries of the detergent ingredients or by dry-mixing processes.

The invention is further illustrated by way of Example.

EXAMPLE I

Preparation of hexasodium tartaric acid dimalonyl ether (TDM)

Dimethyl tartrate (3.53 g, 19.9 mmoles) and activated copper powder (190 mg) were added to a two-necked round bottom flask (25 ml) equipped with a reflux condenser and a serum cap. A plastic tube was attached at the top of the reflux condenser. The plastic tube led via a drying tube to the base of an inverted measuring cylinder, full of water, supported in a water bath. The mixture was stirred vigorously and at about 105° C dimethyl diazomalonate (7.05 g, 44.5 mmole) was added with the aid of an injection syringe the needle of which had been put through the serum cap. Nitrogen gas was evolved and trapped in the measuring cylinder. When the theoretical volume of nitrogen required for complete reaction of the dimethyl diazomalonate had been collected (25 min.) the reaction mixture was cooled. The copper powder was removed by filtration and washed twice with methyl acetate (2 ml). The combined filtrate and washings were then evaporated in vacuo to remove methyl acetate solvent. A colourless liquid residue (9.3 g) was obtained.

*A. I. Vogel, A text-book of practical organic chemistry, 3rd edition, 1964, page 192

9.2 g of this residue was placed on top of a column of acid washed silicagel (Mallinckrodt cc-4, 450 g, 270–325 mesh) made up in chloroform in a chromic acid washed chromatography column (90 × 4 cm). Fractions (15 ml) were collected with the help of a fraction collector (ex LKB-Produkter AB, Stockholm, Sweden; LKB Ultrorac fraction collector type 7000) using a gradient elution technique starting with ethanol-free chloroform as the eluent and slowly increasing the concentration of methyl acetate in it in the usual way. The fractions containing pure (>95%, checked by NMR) hexamethyl TDM were combined (3.1 g).

Analytical data (TDM hexamethyl ester)

IR-spectrum (film): 1755 cm$^{-1}$, broad ($\gamma$CC); 1440 cm$^{-1}$($\delta$CH$_3$, in —OCH$_3$); 1285, 1240, 1160 and 1025 cm$^{-1}$ ($\gamma$C—O—C, ester); 1125 cm$^{-1}$ ($\gamma$C—O—C, ether).

NMR spectrum

The proton magnetic resonance spectrum was obtained at 40° C, using a Varian A-60 spectrometer operating at 60 MHz.

$\delta$-values are quoted in ppm downfield from internal TMS and are accurate to within ± 0.01 ppm.

| | $\delta$ ppm | Multiplicity | Assignment |
|---|---|---|---|
| (structure) | 3.80 | singlet | a |
| | 4.76 | singlet | b |
| | 4.95 | singlet | c |
| | | | solvent CDCl$_3$ |

Mass-Spectrum

Peak intensities are given with the following restrictions:
a. Up to m/e 350 only peaks with intensities > 5%, and
b. over m/e 350 also small peaks which are still characteristic, are given.

| m/e | I | m/e | I | m/e | I | m/e | I |
|---|---|---|---|---|---|---|---|
| 18 | 5.5 | 104 | 12.2 | 189 | 5.3 | 263 | 10.7 |
| 28 | 32.7 | 113 | 18.6 | 191 | 18.0 | 290 | 5.6 |
| 32 | 5.7 | 115 | 6.8 | 201 | 14.5 | 291 | 11.9 |
| 45 | 5.4 | 131 | 6.5 | 203 | 7.9 | 319 | 17.7 |
| 59 | 20.4 | 132 | 18.0 | 217 | 5.0 | 347 | 9.5 |
| 69 | 7.4 | 133 | 5.9 | 219 | 92.8 | 351 | 6.1 |
| 73 | 10.4 | 145 | 15.6 | 220 | 8.5 | 379 | 13.1 |
| 75 | 54.0 | 146 | 6.1 | 231 | 9.5 | 394 | 0.4 |
| 85 | 8.2 | 159 | 8.5 | 233 | 11.6 | 406 | 0.1 |
| 100 | 8.1 | 161 | 13.7 | 247 | 8.9 | 438 | 0.1 |
| 101 | 13.1 | 171 | 5.3 | 258 | 6.3 | 439 | 0.2 |
| 103 | 100 | 175 | 6.8 | 259 | 7.7 | | |

Hexamethyl TDM (5.3 g; 12.1 mmoles) was stirred at room temperature in 1 N aqueous hydrochloric acid (145 ml) under an atmosphere of helium until the solid material dissolved (4½ h). The solution was neutralized with 10 N aqueous sodium hydroxide solution (15 ml) whereupon an excess of sodium hydroxide solution (15 ml; 10 N) was added; subsequently the solution was stirred for 20 h at room temperature under an atmosphere of helium.

The excess of sodium hydroxide was neutralized with acid form ion exchange resin (Dowex AG 50W-X8). After the ion exchange resin was filtered off the filtrate was evaporated to a concentrated solution in vacuo. To this solution a concentrated aqueous solution of excess CaCl$_2$ was slowly added under stirring. The precipitated white calcium salt of TDM was filtered off, washed with water and then converted to the acid with the help of an excess of acid form ion exchange resin (Dowex AG 50W-X3). The ion exchanger was filtered off and the filtrate was neutralized with aqueous sodium hydroxide solution (to the null point of phenol phthalein indicator). Evaporation of the aqueous solution to dryness gave a solid residue of hexasodium TDM. The compound was dried overnight at 70° C/10 mm Hg. The yield was 6.3 g. According to quantitative NMR analysis the product consisted of 90.6 wt.% TDM and 9.3 wt.% H$_2$O.

Analysis (TDM hexasodium salt)

NMR-spectrum

Conditions as mentioned for the NMR-spectrum of TDM hexamethyl ester (internal standard TSS). The coupling constants are accurate to within ± 0.2 Hz.

| ppm | Multiplicity | Assignment |
|---|---|---|
| 4.13 | singlet | a |
| 4.28 | singlet | b |
| | | solvent $D_2O$ |

[Structure: tetrasodium salt with Na—O—C(=O)—CH(a)—O—CH(b)— linkages showing (a)HC—O—CH(b), C—O—Na groups, with second unit (a)HC—O—CH(b), Na—O—C, C—O—Na]

It was not possible to determine the melting point of this product; under nitrogen as well as in vacuo it started decomposing at about 200° C.

EXAMPLE II

Preparation of tetrasodium ethylene glycol disuccinyl ether (EGDS)

Tetraethyl EGDS has been prepared according to the method described in Example I from diethyl diazosuccinate (11.6 g; 58 mmoles) and ethylene glycol (0.89 g; 14.3 mmoles). The nitrogen evolved was 99% of the theroetical value. A liquid residue was obtained (9.7 g).

9.6 g of this liquid was chromatographed over a silica gel column (Mallinckrodt cc-4, 450 g; 200–235 mesh; 90 × 4 cm). Elution (20 ml fractions) has been effected as mentioned in Example I. The fractions containing more than 90% (checked by NMR) of tetraethyl ethylene glycol disuccinate were combined (4.4 g).

Analytical data (EGDS tetraethyl ester)

NMR-spectrum

The conditions were as mentioned in Example I for the NMR-spectrum of TDM hexamethyl ester.

[Structure of tetraethyl EGDS: $CH_3$—$CH_2$O (a)(e) groups with HC—O—$CH_2$—$CH_2$—O—CH linkage (g)(d)(d)(g), $CH_2$(c) and $CH_3$—$CH_2$O (b)(f) groups, ester linkages O$CH_2$—$CH_3$ (e)(a) and O$CH_2$—$CH_3$ (f)(b)]

| δ ppm | Multiplicity | JHz | Assignment |
|---|---|---|---|
| 1.23 | triplet | 7.0 | a or b |
| 1.26 | triplet | 7.0 | b or a |

-continued

[Structure continued, same tetraethyl EGDS]

| δ ppm | Multiplicity | JHz | Assignment |
|---|---|---|---|
| 2.71 | broadened doublet | ca. 6.3c/g | c |
| 3.4–3.8 | complex | — | d |
| 4.09 | quartet | 7.0 | e or f |
| 4.15 | quartet | 7.0 | f or e |
| 4.28 | triplet, partially overlapped by e and f | ca. 6.3 g/c | g |

Solvent: $CDCl_3$

Mass spectrum

Peak intensities are given with the following restrictions:
a. Up to m/e 150 all peaks with intensities > 5%.
b. Over m/e 150 all peaks with intensities > 1%.

| m/e | intensity | m/e | int. | m/e | int. | m/e | int |
|---|---|---|---|---|---|---|---|
| 18 | 7.6 | 128 | 5.4 | 174 | 1.4 | 241 | 2.1 |
| 28 | 17.6 | 143 | 32.7 | 175 | 2.9 | 259 | 2.4 |
| 29 | 14.0 | 145 | 5.6 | 185 | 1.6 | 287 | 100.0 |
| 45 | 7.8 | 157 | 2.1 | 187 | 2.0 | 288 | 14.4 |
| 59 | 14.7 | 159 | 1.8 | 189 | 3.0 | 289 | 2.6 |
| 71 | 5.9 | 161 | 10.1 | 203 | 4.4 | 333 | 7.4 |
| 73 | 33.8 | 167 | 5.7 | 213 | 6.4 | 334 | 1.3 |
| 99 | 11.2 | 168 | 1.1 | 214 | 1.5 | 360 | 3.1 |
| 101 | 8.5 | 170 | 4.0 | 216 | 14.7 | 406 | 1.0 |
| 115 | 6.3 | 171 | 4.2 | 217 | 91.4 | | |
| 117 | 10.4 | 172 | 2.2 | 218 | 10.1 | | |
| 127 | 7.6 | 173 | 4.2 | 219 | 1.7 | | |

Hydrolysis

To 4.4 g of tetraethyl EGDS 125 ml ion exchange resin (Dowex AG 50W-X8) and 50 ml water were added. The mixture was stirred for 48 h at 60° C. The ion exchanger was filtered off at room temperature and washed with water until acid free. After combining the filtrate and washings the solution was neutralized with aqueous sodium hydroxide solution (indicator phenol phthalein). Evaporation of the aqueous solution was followed by drying of the residue overnight at 70° C in vacuo. A light yellow solid residue was obtained (3.8 g). NMR analysis indicated that the product consisted of tetrasodium EGDS and ~ 10 wt.% $H_2O$.

EXAMPLES III–X

The following compounds of the invention were prepared in a manner analogous to that of Examples I and II, and their NMR-spectra were measured.

PGDM (tetrasodium salt)

-continued (a) CH$_3$
(c) HC—O—CH (d) —C(=O)—ONa, —C(=O)—ONa
(b) H$_2$C—OCH(e) —C(=O)—ONa, —C(=O)—ONa

| δ ppm | Multiplicity | JHz | Assignment |
|---|---|---|---|
| 1.16 | doublet | 6.3 | a |
| 3.3–4.1 | complex | — | b+c |
| 4.24 | singlet** | — | d |
| 4.40 | singlet | — | e |

**Tentative assignment after comparison with proton c of the spectrum of EGAM.

TEGDM (tetrasodium salt)

NaO—C(=O)—(b)HC—O—CH$_2$—CH$_2$—O—CH$_2$—CH$_2$—O—CH$_2$—CH$_2$—O—CH(b)—C(=O)—ONa
             (a)   (a)    (a)   (a)    (a)   (a)
NaO—C(=O)—                                            —C(=O)—ONa

| δ ppm | Multiplicity | JHz | Assignment |
|---|---|---|---|
| 3.5–3.9 | complex | — | a |
| 4.24 | singlet | — | b |

PGDS (tetrasodium salt)*

(a) H$_3$C
(d) HC—O—CH(e)—CH$_2$(b)—C(=O)—ONa, —C(=O)—ONa
(c) H$_2$C—O—CH(e)—CH$_2$(b)—C(=O)—ONa, —C(=O)—ONa

| δ ppm | Multiplicity | JHz | Assignment |
|---|---|---|---|
| 1.18 | complex | — | a |
| 2.54 | complex | — | b |
| 3.3–4.4 | complex | — | c+d+e |

PGMcS (disodium salt)

(a) CH$_3$
(c) HC—OH
(d) H$_2$C—O—CH(e)—CH$_2$(b)—C(=O)—ONa, —C(=O)—ONa

| δ ppm | Multiplicity | JHz | Assignment |
|---|---|---|---|
| 1.12 | doublet | 6.5 | a |
| 2.56 | AB part of ABX system | — | b |
| 3.3–4.3 | complex | — | c+d+e |

-continued

DEGDS (tetrasodium salt)

```
     O                                              O
      \\                                           //
       C                                          C
      /  |                                        |  \
   NaO   |                                        |   ONa
     (c) HC—O—CH₂—CH₂—O—CH₂—CH₂—O—CH (c)
            (b)  (b)    (b)  (b)
     (a) H₂C                                 CH₂ (a)
          O                                   O
           \\                               //
            C                              C
           /                                \
        NaO                                  ONa
```

| δ ppm | Multiplicity | JHz | Assignment |
|---|---|---|---|
| 2.56 | AB part of ABX system | — | a |
| 3.72 | broadened singlet | — | b |
| 4.13 | X part of ABX system | 8.5; 4.6 | c |

DEGMoS (disodium salt)

```
                                       O
                                       //
                                      C
                                       \
                                        ONa
                                       |
   HOCH₂—CH₂—O—CH₂—CH₂—O—CH (c)
     (b)   (b)   (b)  (b)       |
                                CH₂ (a)
                                 O
                                  \\
                                   C
                                    \
                                     ONa
```

| δ ppm | Multiplicity | JHz | Assignment |
|---|---|---|---|
| 2.52 | AB part of ABX system | — | a |
| 3.5–3.9 | complex | — | b |
| 4.13 | X part of ABX system | 9.0; 4.5 | c |

DGMoS (disodium salt)

```
                         O
                         //
                        C
                         \
                          ONa
                         |
   HO—CH₂—CH₂—O—CH (c)
      (b)   (b)    |
                   CH₂ (a)
                    O
                     \\
                      C
                       \
                        ONa
```

| δ ppm | Multiciplicity | JHz | Assignment |
|---|---|---|---|
| 2.56 | AB part of ABX system | — | a |
| 3.70 | broadened singlet | — | b |
| 4.11 | X part of ABX system | 8.0; 4.8 | c |

EGAM (trisodium salt)

```
     O                           O
      \\                        //
       C                       C
      /  |                     |  \
   NaO   |                     |   ONa
     (b)H₂C—O—CH₂—CH₂—O—CH (c)
              (a)   (a)    |
                            O
                             \\
                              C
                               \
                                ONa
```

| δ ppm | Multiplicity | JHz | Assignment |
|---|---|---|---|
| 3.69 | broadened singlet | — | a |
| 3.98 | singlet | — | b |
| 4.24 | singlet | — | c |

*The compounds marked with * are mixtures of diastereoisomers. This makes the NMR-spectra more complicated.

The (dicarboxy)alkyl ethers are useful as builders in detergent compositions. This is exemplified by washing experiments, in which the detergency of detergent compositions, containing either sodium tripolyphosphate, or various (dicarboxy)alkyl ethers according to the invention, was determined in Tergotometer tests, using artificially soiled cotton cloth test pieces, known under codes AS 8 and AS 12 and VCD. The detergent composition used contained the following ingredients:

| | % by weight |
|---|---|
| sodium dodecylbenzenesulphonate | 5 |

| | % by weight |
|---|---|
| sodium hardened tallow soap | 6 |
| dinonylphenol condensed with 16 moles of ethylene oxide | 3 |
| nonylphenol condensed with 10 moles of ethylene oxide | 1 |
| sodium silicate | 7 |
| sodium sulphate | 14 |
| sodium carboxymethylcellulose | 0.5 |
| ethylenediaminetetraacetic acid | 0.2 |
| sodium perborate | 22 | and furthermore one of the following builders:
- a sodium tripolyphosphate (STP) 30% by weight
- b sodium TDM equivalent to STP mol/mol ratio
- c sodium PGDM equivalent to STP mol/mol ratio
- d sodium TEGDM equivalent to STP mol/mol ratio
- e sodium EGDS equivalent to STP mol/mol ratio
- f sodium PGDS equivalent to STP mol/mol ratio
- g sodium DEGDS equivalent to STP mol/mol ratio
- h sodium EGAM 30% by weight The conditions of the detergency test were:

| Speed | 75 spm |
|---|---|
| Time-temp. | from 25 to 90° C in 45 min.; 5 min. at 90° C |
| Test cloth | AS 8; AS 12 and VCD |
| Cloth/liquor ratio | 1:50 |
| Water hardness | 10° GH (Ca$^{++}$:Mg$^{++}$=4:1) |
| Concentration | 3 g detergent/l. |

The detergency results were:

Washing efficiency (%)

| | TDM | STP | PGDM | STP | TEGDM | STP | EGDS | STP | PGDS | STP | DEGDS | STP | EGAM | STP |
|---|---|---|---|---|---|---|---|---|---|---|---|---|---|---|
| AS 8 | 65.2 | 65.1 | 67.9 | 71.3 | 63.3 | 67.8 | 67.8 | 61.9 | 61.9 | 65.1 | 63.0 | 65.1 | 61.7 | 67.8 |
| As 12 | 77.6 | 77.3 | 71.1 | 73.5 | 74.1 | 79.4 | 76.4 | 79.4 | 75.5 | 77.3 | 74.5 | 77.3 | 73.1 | 79.4 |
| VCD | 53.4 | 51.0 | 53.3 | 50.2 | 43.9 | 54.0 | 50.0 | 54.0 | 47.4 | 51.0 | 48.6 | 51.0 | 45.5 | 54.0 |

*RW—Rs/Rc—Rs × 100%
Rw is the reflectance reading of washed testcloth
Rs is the reflectance reading of unwashed testcloth
Rc is the reflectance reading of clean testcloth The figures are the average values of two experiments.

We claim:
1. Novel tartaric acid dimalonyl ethers, useful as builders in detergent compositions, of the following formula:

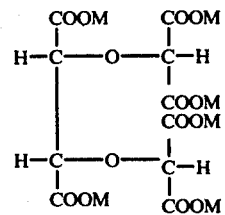

in which M = H, —CH$_3$, —C$_2$H$_5$, Na or K.

* * * * *